United States Patent [19]

Ishikawa et al.

[11] Patent Number: 5,075,308

[45] Date of Patent: Dec. 24, 1991

[54] METHOD FOR TREATING URINARY OBSTRUCTION

[75] Inventors: Masayuki Ishikawa, Tokyo; Hiroshi Azuma, Asaka; Shigeru Ito, Yokohama, all of Japan

[73] Assignee: Hitachi Chemical Co., Ltd., Tokyo, Japan

[21] Appl. No.: 480,237

[22] Filed: Feb. 15, 1990

[30] Foreign Application Priority Data

Aug. 31, 1989 [JP] Japan .................................. 1-223073

[51] Int. Cl.$^5$ ..................... A61K 31/50; A61K 31/495
[52] U.S. Cl. ...................................................... 514/252
[58] Field of Search ........................................ 514/252

[56] References Cited

FOREIGN PATENT DOCUMENTS 40229 9/1986 Japan .
51672 3/1987 Japan .
26517 7/1989 Japan .

OTHER PUBLICATIONS

Iyaku Journal, vol. 24, No. 12, p. 2661 (1988).
Nihon Hinyoki Gakkai-shi, vol. 76, 325-327 (1985).
Iyaku to Yakugaku, vol. 19, 411 ∝ 429 (1988).

*Primary Examiner*—Leonard Schenkman
*Attorney, Agent, or Firm*—Abelman Frayne & Schwab

[57] ABSTRACT

A method for treating urinary obstruction by administering a 2-(4-phenyl-1-piperazinylalkyl)aminopyrimidine derivative represented by the formula

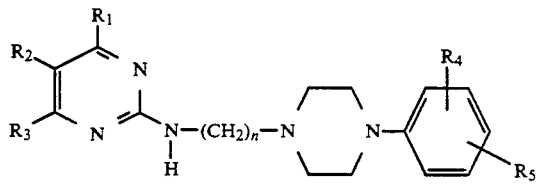

wherein $R_1$ and $R_3$ may be the same or different and independently represent hydrogen, halogen, an amino group, a hydroxyl group, a straight or branched chain lower alkyl group, a straight or branched chain lower alkoxy group, or a straight or branched chain hydroxy-lower alkyl group, $R_2$ represents hydrogen, halogen, a carboxyl group, a straight or branched chain lower alkyl group, a straight or branched chain lower alkylcarbonyl group, or a straight or branched chain lower alkyloxycarbonyl group, $R_4$ and $R_5$ may be the same or different and independently represent hydrogen, halogen, a straight or branched chain lower alkyl group, or a straight or branched chain lower alkoxy group, and n represents an integer of 2 to 6 or a pharmaceutically acceptable acid addition salt thereof to a mammal including a human afflicted with urinary obstruction. The aminopyrimidine derivatives have a selective activity on the $\alpha_1$-adrenoceptors in the urinary tracts.

3 Claims, 1 Drawing Sheet

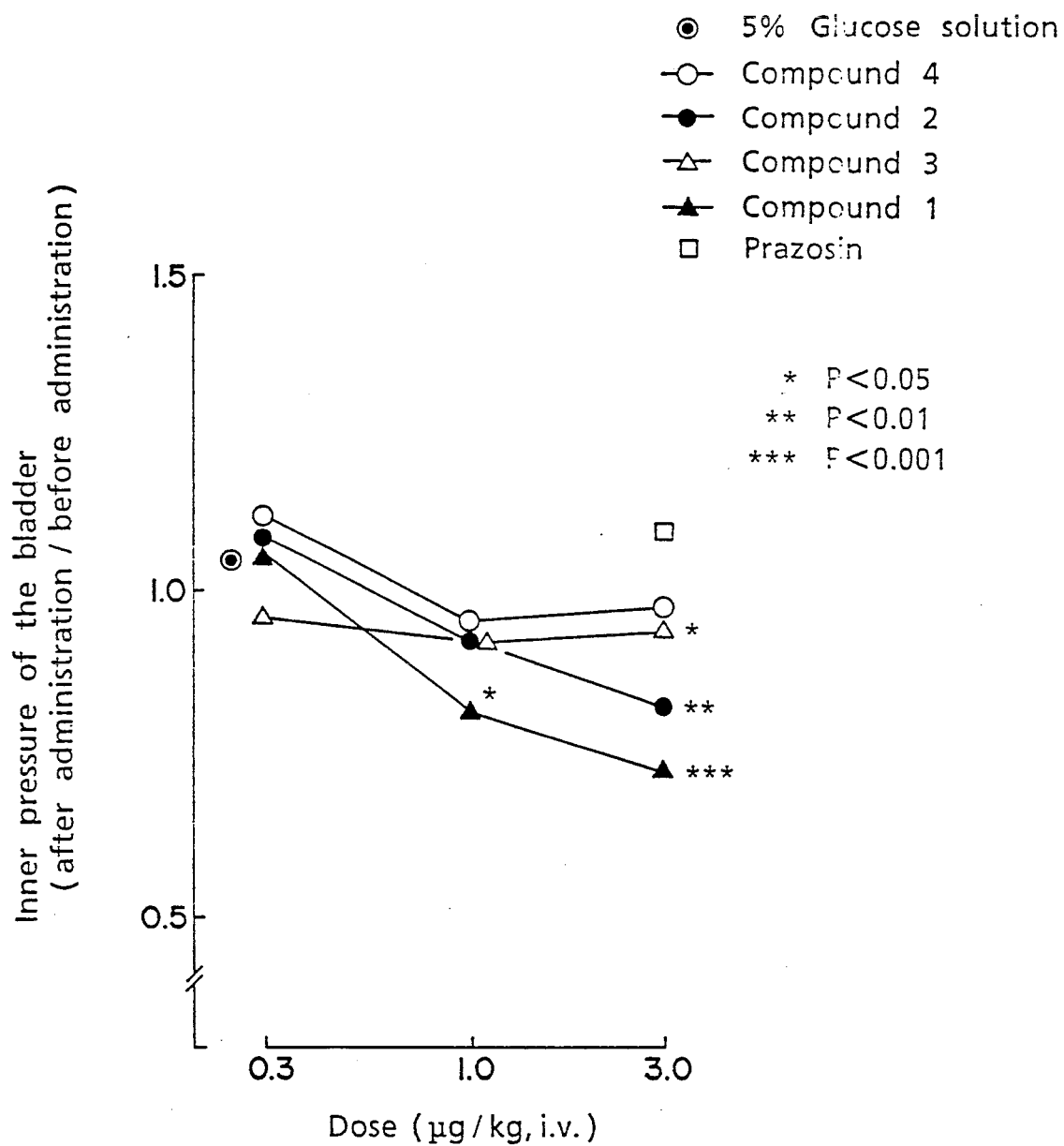
F/G. /

METHOD FOR TREATING URINARY OBSTRUCTION

BACKGROUND OF THE INVENTION

1. Field of the Invention

This invention relates to a method for treating urinary obstruction which comprises administering a therapeutically effective amount of a 2-(4-phenyl-l-piperazinylalkyl)-aminopyrimidine derivative or a pharmaceutically acceptable acid addition salt thereof to mammal including a human afflicted with urinary obstruction.

2. Description of Prior Art

Urinary obstruction includes such symptoms as difficulty in urination, pollakiuria, nocturnal enuresis, incontinence of urine, feeling of residual urine and acute ischuria. These symptoms occur due to a variety of causes, for example, hypertrophy of prostate glands, autonomic imbalance, organic deficiencies of the urinary tracts or nephritis and cystitis caused by infectious microorganisms.

It has been revealed that the urinary obstruction caused by hypertonia of the sympathetic nervous system and prostatauxe among those mentioned above is deeply related to the contraction of smooth muscles via $\alpha_1$-adrenoceptors (for example, Yamaguchi et al.: Iyaku Journal, Vol. 24, No. 12, 1988, p. 2661).

As for hypertrophy of the prostate glands in humans, it is suggested that increase in distribution density of $\alpha_1$-adrenoceptors promotes resistance to urination, because there is observed no change of the sensitivity of $\alpha_1$-adrenoceptors in the prostate glands but marked increase in their distribution density in proportion to hypertrophy of the prostate glands (Yokoyama et al.: Nihon Hinyoki Gakkai-shi, Vol. 76, pp. 325–327, 1985).

Further, efficacy of prazosin which has already been used as an $\alpha_1$-adrenoceptor blocking agent in antihypertensives is clinically evaluated and is being recognized as a therapeutic agent for the urinary obstruction caused by hypertrophy of prostate glands or hypertonia of the sympathetic nervous system (Yamaguchi et al.: Iyaku to Yakugaku, Vol. 19, pp. 411–429, 1988).

Furthermore, certain prazosin-analogous compounds which exhibit a mild antihypertensive action (Japanese Patent Publication No. 40229/1986) have been found to possess an $\alpha_1$-adrenoceptor blocking activity at those sites which play an important role in urination mechanism, and it is proposed that they will be useful not only as a hypotensive agent but also as a therapeutic agent for 26517/1989).

However, since these $\alpha_1$-adrenoceptor blocking agents are poorly selective in that they block not only $\alpha_1$-adrenoceptors in tissues of the urinary tracts which play an important role in urination mechanism but also $\alpha_1$-adrenoceptors distributed in blood vessels, there still remain problems of adverse reactions such as orthostatic hypotensive asthenia.

Therefore, $\alpha_1$-adrenoceptor blocking agents which are less active on the $\alpha_1$-adrenoceptors distributed in blood vessels but highly active on the $\alpha_1$-adrenoceptors distributed in the lower urinary tracts, for example, the prostate gland, internal urethral sphicter muscle and trigonum vesicae would be useful as agents for treating urinary obstruction without fear of said side effects. In this respect, it is a subject to develop, as a therapeutic agent for urinary obstruction, $\alpha_1$-adrenoceptor blocking agents possessing such properties.

SUMMARY OF THE INVENTION

As a result of extensive studies to solve the above subject we have found that certain 2-(4-phenyl-l-piperazinylalkyl)aminopyrimidine derivatives are selectively active on the $\alpha_1$-adrenoceptors in the urinary tracts and that they are useful as therapeutic agents for urinary obstruction with no fear of the above-mentioned adverse reactions. The present invention is based upon the above findings.

Thus, the invention relates to a method for treating urinary obstruction which comprises administering a therapeutically effective amount of a 2-(4-phenyl-l-piperazinylalkyl)aminopyrimidine derivative represented by formula (I)

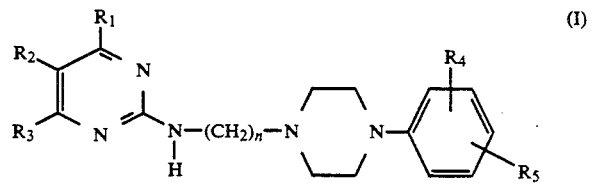

wherein $R_1$ and $R_3$ may be the same or different and independently represent hydrogen, halogen, an amino group, a hydroxyl group, a straight or branched chain lower alkyl group, a straight or branched chain lower alkoxyl group, or a straight or branched chain hydroxylower alkyl group, $R_2$ represents hydrogen, halogen, a carboxyl group, a straight or branched chain lower alkyl group, a straight or branched chain lower alkylcarbonyl group, or a straight or branched chain lower alkyloxycarbonyl group, $R_4$ and $R_5$ may be the same or different and independently represent hydrogen, halogen, a straight or branched chain lower alkyl group, or a straight or branched chain lower alkoxy group, and n represents an integer of 2 to 6 or a pharmaceutically acceptable acid addition salt thereof.

BRIEF DESCRIPTION OF THE DRAWING

FIG. 1 shows relationship between the ratio of the inner pressure of the bladder before administration of the test drug to that after administration and the dose of the drug.

DETAILED DESCRIPTION OF THE INVENTION

The above-mentioned 2-(4-phenyl-l-piperazinylalkyl)aminopyrimidine derivatives of formula (I) are known compounds which were presented by us in Japanese Patent LOP Publication No. 51672/1987 as a therapeutic agent for hypertension and also as a cerebral circulation-improving agent such as a blood flow-improving agent for peripheral blood flow disturbance, ischemic cerebral impairment or cerebral thrombosis. It is however a new finding that the compounds are selectively active on the $\alpha_1$-adrenoceptors in tissues of the urinary tracts and are useful as a therapeutic agent for urinary obstruction.

The above-mentioned 2-(4-phenyl-l-piperazinylalkyl)aminopyrimidine derivatives of formula (I) were tested by us for the $\alpha_1$-adrenoceptor blocking activity both in blood vessels and in the lower urinary tracts. We have compared these activities and investigated tissue-selectivity of the $\alpha_1$-adrenoceptor blocking activity. As a result of the investigation the above-mentioned compounds are found to possess a blocking activity selectively on the $\alpha_1$-adrenoceptors distributed in the lower urinary tracts. Therefore, unlike prior $\alpha_1$-adrenoceptor blocking agents such as prazosin used as a therapeutic agent for urinary obstruction, the above-mentioned compounds can be used as a therapeutic agent for urinary obstruction free from side effects such as orthostatic hypotensive asthenia.

According to the disclosure in Japanese Patent LOP Publication No. 51672/1987, the 2-(4-phenyl-l-piperazinylalkyl)aminopyrimidine derivatives of the above-mentioned formula (I) are produced by reacting a pyrimidine derivative of formula (II)

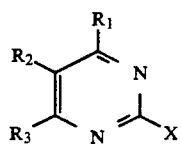

wherein $R_1$, $R_2$ and $R_3$ have the same meaning as defined above and X means a halogen atom and a 4-phenyl-l-piperazinylalkylamine derivative having formula (III)

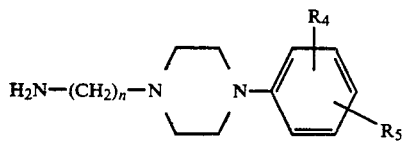

wherein $R_4$, $R_5$ and n have the same meaning as above, in the presence or absence of a base and, if needed, converting the product to an acid addition salt.

It is to be noted that the above is only an example of a process for preparing the compounds of formula (I) which can apparently be prepared by other methods.

As particular examples of the halogen for the groups $R_1$ and $R_3$ in the compounds of formula (I) are mentioned fluorine, chlorine, bromine and iodine. As particular examples of straight or branched chain lower alkyl group are mentioned methyl, ethyl, n-propyl, i-propyl, n-butyl, i-butyl, tert-butyl and the like. As particular examples of the straight or branched chain lower alkoxyl group are mentioned methoxy, ethoxy, n-propoxy, i-propoxy, n-butoxy, i-butoxy, tert-butoxy and the like. As particular examples of straight or branched chain hydroxy-lower alkyl group are mentioned hydroxymethyl, hydroxyethyl, hydroxypropyl and the like.

Particular examples of the halogen and the straight or branched chain lower alkyl group for the group $R_2$ in the compounds of formula (I) are the same as those mentioned above for the groups $R_1$ and $R_3$ As particular examples of the straight or branched chain lower alkylcarbonyl group are mentioned acetyl, propionyl, i-propionyl, butyryl, i-butyryl and the like. Particular examples of the straight or branched chain lower alkyl group of the straight or branched chain lower alkyloxycarbonyl are the same as those mentioned above for the groups $R_1$ and $R_3$.

Particular examples of the halogen, the straight or branched chain lower alkyl group and the straight or branched chain lower alkoxy group for the groups $R_4$ and $R_5$ of formula (I) are the same mentioned for the groups $R_1$ and $R_3$.

As particular examples of the compound of formula (I) are mentioned.

2-[2-(4-(2-methoxyphenyl)-l-piperazinyl)ethyl]amino-5-acetyl-4,6-dimethylpyrimidine, 2-[2-(4-(2-methoxyphenyl)-l-piperazinyl)ethyl]amino-5-ethoxycarbonyl-4,6-dimethylpyrimidine, 2-[4-(4-(2-methoxyphenyl)-l-piperazinyl)butyl]amino-5-ethoxycarbonyl-4,6-dimethylpyrimidine, 2-[3-(4-(2-methoxyphenyl)-l-piperazinyl)propyl]amino-4,6-dimethylpyrimidine, 2-[2-(4-(2-methoxyphenyl)-l-piperazinyl)ethyl]amino-4-chloropyrimidine, 2-[2-(4-(2-methoxyphenyl)-l-piperazinyl)ethyl]aminopyrimidine, 2-[2-(4-(2-methoxyphenyl)-l-piperazinyl)ethyl]amino-4-methoxypyrimidine, 2-[4-(4-(2-methoxyphenyl)-l-piperazinyl)butyl]amino-4-methoxypyrimidine, 2-(2-(4-phenyl-l-piperazinyl)ethyl)amino-5-ethoxycarbonyl-4,6-dimethylpyrimidine, 2-[2-(4-(2-chlorophenyl)-l-piperazinyl)ethyl]amino-5-ethoxycarbonyl-4,6-dimethylpyrimidine, 2-[2-(4-(4-chlorophenyl)-l-piperazinyl)ethyl]amino-5-ethoxycarbonyl-4,6-dimethylpyrimidine, 2-[2-(4-(2-methylphenyl)-l-piperazinyl)ethyl]amino-5-ethoxycarbonyl-4,6-dimethylpyrimidine, 2-[2-(4-(3-methoxyphenyl)-l-piperazinyl)ethyl]amino-5-ethoxycarbonyl-4,6-dimethylpyrimidine, 2-[2-(4-(4-methoxyphenyl)-l-piperazinyl)ethyl]amino-5-ethoxycarbonyl-4,6-dimethylpyrimidine, 2-[2-(4-(2,4-dimethoxyphenyl)-l-piperazinyl)ethyl]amino-5-ethoxycarbonyl-4,6-dimethylpyrimidine, 2-[2-(4-(3,4-methylenedioxyphenyl)-l-piperazinyl)ethyl]amino-5-ethoxycarbonyl-4,6-dimethylpyrimidine, 2-[3-(4-(2-methoxyphenyl)-l-piperazinyl)propyl]amino-5-ethoxycarbonyl-4,6-dimethylpyrimidine, 2-[2-(4-(2-methoxyphenyl)-l-piperazinyl)ethyl]amino-4,6-dimethylpyrimidine, 2-[2-(4-(2-methoxyphenyl)-l-piperazinyl)ethyl]amino-5-bromo-4,6-dimethylpyrimidine, 2-[2-(4-(2-methoxyphenyl)-l-piperazinyl)ethyl]amino-5-carboxy-4,6-dimethylpyrimidine, 2-[2-(4-(2-methoxyphenyl)-l-piperazinyl)ethyl]amino-4-aminopyrimidine, 2-[2-(4-(2-methoxyphenyl)-l-piperazinyl)ethyl]amino-4-benzyloxypyrimidine, and the like. These compounds may also be employed as a pharmaceutically acceptable acid addition salt.

As the acid addition salts are mentioned, for example, mineral acid salts such as hydrochloride, sulfate, hydrobromide and phosphate and organic acid salts such as oxalate, acetate, lactate, succinate, citrate, tartrate, maleate, fumarate and malate.

The agent for treating urinary obstruction according to the invention can be administered orally, for example, as tablets, capsules, granules, powders or syrup, parenterally as suppositories, by intravenous or subcutaneous injection of a injectable preparation, or percutaneously, as ointment.

The tablets are prepared by compressing or forming the active ingredient together with additional adjuvant components. As the adjuvant component may be used pharmaceutically acceptable excipients such as binders (e.g. corn starch), fillers (e.g. lactose, microcrystalline cellulose), disintegrating agents (e.g. sodium starchglycolate), or wetting agents (e.g. sodium laurate). The tablets may also be coated.

Liquid preparations such as syrup, solution or suspension can be prepared by a conventional method, for example, using a suspending agent (e.g. methylcellulose), an emulsifier (e.g. lecithin) or a preservative.

The injectable preparation may be in the form of solution, suspension, or oily or aqueous emulsion and may contain a suspension stabilizer, a dispersing agent or the like.

Although a dosage of the drug is variable depending upon the administering form, symptoms, age and body weight of the patient and the compound to be used, it is preferable in oral administration to give 0.1 mg-300 mg per day in 1-3 divided doses in adults.

In the examples are shown the results of the test on particular compounds of formula (I) of the invention for the selectively blocking activity on $\alpha_1$-adrenoceptors distributed in the lower urinary tracts and the urination-promoting activity in order to demonstrate that these particular compounds can effectively be used in the therapy of urinary obstruction resulted from hyperactivity of $\alpha_1$-adrenoceptors in the lower urinary tracts without accompanying adverse reactions such as orthostatic hypotensive asthenia.

Particular compounds of formula (I) used in the examples are listed in Table 1.

In the examples, prazosin, a known drug, is used as a comparative compound.

TABLE 1

Particular test compounds

| Compound | $R_1$ | $R_2$ | $R_3$ | $R_4$ | $R_5$ | n |
|---|---|---|---|---|---|---|
| Compound 1 | $CH_3$ | $COCH_3$ | $CH_3$ | 2-$OCH_3$ | H | 2 |
| Compound 2 | $CH_3$ | $CO_2C_2H_5$ | $CH_3$ | 2-$OCH_3$ | H | 4 |
| Compound 3 | $CH_3$ | H | $CH_3$ | 2-$OCH_3$ | H | 2 |
| Compound 4 | $CH_3$ | $CO_2C_2H_5$ | $CH_3$ | 2-$OCH_3$ | H | 3 |
| Compound 5 | H | H | Cl | 2-$OCH_3$ | H | 2 |
| Compound 6 | H | H | H | 2-$OCH_3$ | H | 2 |
| Compound 7 | $CH_3$ | $CO_2C_2H_5$ | $CH_3$ | 2-$OCH_3$ | H | 2 |
| Compound 8 | H | H | $OCH_3$ | 2-$OCH_3$ | H | 2 |
| Compound 9 | H | H | $OCH_3$ | 2-$OCH_3$ | H | 4 |

EXAMPLE 1

Comparison of $\alpha_1$-adrenoceptor-blocking activity in the smooth muscle of trigonum vesicae and thoracic aorta among test drugs Male albino rabbits weighing 2.2-2.5 kg were intravenously given pentobarbital (Nembutal ®) manufactured by Abbott) at a dose of 35 mg/kg body weight and sacrificed by exsanguination. The thoracic aorta and urinary bladder were rapidly excised and placed in modified Krebs solution. After removal of fat and unnecessary connective tissue, helical strips (3×15 mm in size) of the thoracic aorta and longitudinal strips (3×15 mm in size) of trigonum vesicae were prepared and used as specimen. The helical strips were carefully denuded of endothelium attached thereto in order to avoid any effect of the endothelium-derived vascular relaxing factors.

The preparations were vertically mounted in an organ bath filled with 20 ml of the modified Krebs solution (aerated with a gas mixture of 95 vol % of oxgen and 5 vol % of carbon dioxide and kept at 37° C.). The other end of each strip was attached to a transducer for tension measurement (the model TB-611T manufactured by Nihon Kohden Kogyo K.K.). Changes in tension were recorded on a pen-writing oscillograph (the model Wi-681G manufactured by Nihon Kohden Kogyo K.K.). Composition of the modified Krebs solution used herein was as follows: NaCl 115.0, KCl 4.7, $MgSO_4.7H_2O$ 1.2, $CaCl_2.2H_2O$ 2.5, $KH_2PO_4$ 1.2, $NaHCO_3$ 25.0 and glucose 10.0 (concentration in mM). The solution contained $10^{-6}$ M propranolol, a $\alpha$-adrenoceptor blocker (manufactured by Sigma). The loading tension was adjusted to attain a weight of 2 g for aorta and a weight of 1 g for trigone. The strips were allowed to equilibrate for at least 60 min. before initiation of the experiment, and during this period the modified Krebs solution in the organ bath was replaced every 20 min.

First, noradrenaline (manufactured by Sigma, $10^{-6}$-$10^{-4}$ M) was cumulatively added to each specimen to prepare a concentration-response curve to noradrenaline (to determine the 50% effective concentration $ED_{50}$). Next, in order to assess the $\alpha_1$-adrenoceptor-blocking activity of various drugs, noradrenaline was cumulatively added in the same way as above to each specimen in the presence of one of the compounds 1-9 listed in Table 1, or in the presence of prazosin as a control drug to prepare a concentration-response curve to noradrenaline. The results were analyzed by Schild plotting to determine $pA_2$ (reciprocal of the log of concentration of the blocking agent necessary for parallel shift of the 50% contraction caused by noradrenaline to a concentration two fold as high). The results are shown in Table 2.

Any of the compounds of formula (I) exhibited a larger $pA_2$ in trigonum vesicae. In other words, the noradrenaline contraction was inhibited in a lower concentration. On the contrary, the $pA_2$ was smaller in the thoracic aorta. Thus, as the noradrenaline contraction is inhibited in the thoracic aorta only in a relatively high concentration, it can be said that selectivity of these drugs toward trigonum vesicae is 1.8-6.8 times higher than that toward the thoracic aorta.

It is noted that prazosin shows a larger $pA_2$ in the thoracic aorta than in the trigonum vesicae, and consequently shows higher selectivity in the thoracic aorta than in trigonum vesicae.

TABLE 2

Comparative selectivity of the $\alpha_1$-adrenoceptor blocking activity

| | $pA_2$* | | |
|---|---|---|---|
| Compound | Thoracic aorta | Trigonum vesicae | Activity ratio** |
| Compound 1 | 7.35 (±0.09) | 8.07 (±0.04) | 5.25 |
| Compound 2 | 7.47 (±0.10) | 8.30 (±0.33) | 6.76 |
| Compound 3 | 7.67 (±0.04) | 8.15 (±0.03) | 3.02 |
| Compound 4 | 7.65 (±0.09) | 8.28 (±0.08) | 4.27 |
| Compound 5 | 7.83 (±0.04) | 8.28 (±0.04) | 2.82 |
| Compound 6 | 7.74 (±0.06) | 8.10 (±0.04) | 2.29 |
| Compound 7 | 7.92 (±0.'2) | 8.26 (±0.08) | 2.19 |
| Compound 8 | 7.92 (±0.08) | 8.19 (±0.04) | 1.86 |

TABLE 2-continued

| | Comparative selectivity of the $\alpha_1$-adrenoceptor blocking activity | | |
|---|---|---|---|
| | pA$_2$* | | |
| Compound | Thoracic aorta | Trigonum vesicae | Activity ratio** |
| Compound 9 | 7.96 (±0.05) | 8.21 (±0.05) | 1.78 |
| Prazosin | 8.55 (±0.02) | 8.22 (±0.04) | 0.47 |

*The result is expressed in terms of the mean value (± standard deviation).
**The activity ratio is expressed in terms of the ratio of pA$_2$ (calculated as concentration in all cases) with trigonum vesicae as specimen to pA$_2$ with the thoracic aorta as specimen.

EXAMPLE 2

Effect of the test drugs on the inner pressure of the bladder on urination

The drugs were tested using rats for the effect on inner pressure changes of the bladder on urination.

Normal male rats weighing 300–400 g were subjected under urethane anesthesia to laparotomy to expose the bladder. A small opening wa formed at the top of the bladder, through which a cannula was inserted and then ligated. The other end of the cannula was bifurcated, and one end of the bifurcation was connected to a pressure transducer to record inner pressure changes of the bladder on a polygraph. Through the other end of the bifurcation was continuously introduced physiological saline solution at a flow rate of 0.05 ml/min. The inner pressure changes of the bladder were recorded from initiation of the continuous introduction of physiological saline solution until the first urination was observed.

The test drugs used herein, that is, the compounds of the invention shown in Table 1 and prazosin for comparison were diluted with 5 w/v % of glucose solution respectively and then administered to the rat via the femoral vein at the same time when the continuous introduction of physiological saline solution was initiated. The ureters had been ligated and cut on the side of the kidneys to avoid influence of the retention of urine.

As clearly shown in FIG. 1, the compounds represented by formula (I) possess an urination-promoting effect.

Since 2-(4-phenyl-l-piperazinylalkyl)aminopyrimidine derivatives represented by the above-mentioned formula (I) or pharmaceutically acceptable acid addition salts thereof possess a selective $\alpha_1$-adrenoceptor-blocking activity which is higher on $\alpha_1$-adrenoceptors distributed in the lower urinary tracts than on those in blood vessels and further exhibit an urination-promoting effect, it is expected that they are useful for the therapy of urinary obstruction resulted from hyperactivity of the $\alpha_1$-adrenoceptors in the lower urinary tracts free from side effects such as orthostatic hypotensive asthenia.

What is claimed is:

1. A method for treating urinary obstruction which comprises administering a therapeutically effective amount of a 2-(4-phenyl-l-piperazinylalkyl)aminopyrimidine derivative represented by the formula

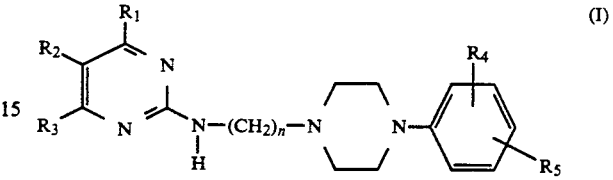

wherein $R_1$ and $R_3$ may be the same or different and independently represent hydrogen, halogen, an amino group, a hydroxyl group, a straight or branched chain lower alkyl group, a straight or branched chain lower alkoxy group, or a straight or branched chain hydroxy-lower alkyl group, $R_2$ represents hydrogen, halogen, a carboxyl group, a straight or branched chain lower alkyl group, a straight or branched chain lower alkylcarbonyl group, or a straight or branched chain lower alkyloxycarbonyl group, $R_4$ and $R_5$ may be the same or different and independently represent hydrogen, halogen, a straight or branched chain lower alkyl group, or a straight or branched chain lower alkoxy group, and n represents an integer of 2 to 6 or a pharmaceutically acceptable acid addition salt thereof to a mammal including a human afflicted with urinary obstruction.

2. A method for treating urinary obstruction according to claim 1 in which the aminopyrimidine derivative is a compound of formula I wherein $R_1$ represents a hydrogen atom or a lower alkyl group, $R_2$ represents a hydrogen atom, a lower alkoxycarbonyl group or a lower alkylcarbonyl group, $R_3$ represents a hydrogen atom, a halogen atom, a lower alkyl group or a lower alkoxy group, $R_4$ represents a lower alkoxy group, $R_5$ represents a hydrogen atom and n represents an integer of 2 to 4.

3. A method for treating urinary obstruction according to claim 1 in which the aminopyrimidine derivative is a compound of formula I wherein $R_1$ represents a hydrogen atom or a methyl group, $R_2$ represents a hydrogen atom, an ethoxycarbonyl group or a methyl carbonyl group, $R_3$ represents a hydrogen atom, a methyl group, a methoxy group or a chlorine atom, $R_4$ represents a methoxy group, $R_5$ represents a hydrogen atom and n represents an integer of 2 to 4.

* * * * *